(12) United States Patent
Dobashi

(10) Patent No.: US 7,556,379 B2
(45) Date of Patent: Jul. 7, 2009

(54) OPHTHALMOLOGIC APPARATUS

(75) Inventor: Yasuhiro Dobashi, Ohta-ku (JP)

(73) Assignee: Canon Kabushiki Kaisha, Tokyo (JP)

( * ) Notice: Subject to any disclaimer, the term of this patent is extended or adjusted under 35 U.S.C. 154(b) by 252 days.

(21) Appl. No.: 11/560,003

(22) Filed: Nov. 15, 2006

(65) Prior Publication Data
US 2007/0115430 A1    May 24, 2007

(30) Foreign Application Priority Data
Nov. 18, 2005   (JP) .............................. 2005-333627

(51) Int. Cl.
*A61B 3/10* (2006.01)
(52) U.S. Cl. ...................... 351/221; 351/206
(58) Field of Classification Search ................. 351/200, 351/206, 210, 221
See application file for complete search history.

(56) References Cited

U.S. PATENT DOCUMENTS

2003/0071966 A1*  4/2003  Matsumoto .................. 351/206

FOREIGN PATENT DOCUMENTS

JP    02-124137 A    5/1990

* cited by examiner

*Primary Examiner*—Huy K Mai
(74) *Attorney, Agent, or Firm*—Canon U.S.A, Inc. IP Division

(57) ABSTRACT

An ophthalmologic apparatus according to an exemplary embodiment of the present invention determines the photography light amount suitable for picking up still images of a fundus and the amplification factor of an image pickup device by obtaining the change in brightness in the fundus.

3 Claims, 4 Drawing Sheets

OPHTHALMOLOGIC APPARATUS

BACKGROUND OF THE INVENTION

1. Field of the Invention

The present invention relates to an ophthalmologic apparatus capable of taking photofluorography.

2. Description of the Related Art

A known photography apparatus, for observing an examinee eye, picks up an image of an examinee eye with an image pickup device, as represented by a CCD, and converts it into an image signal. Since an optical finder cannot be used, especially when taking infrared photofluorography with a fundus camera, alignment and focusing are carried out using an image pickup device.

In general, a radiographic contrasting period of the photofluorography is classified into three stages: a radiographic contrast early phase (1) where the stage is from the starting of contrasting a choroid coat to contrasting a choroidal vein; a radiographic contrast medium phase (2) where the stage is until a fluorescence agent is vanished in the choroidal vein; and a radiographic contrast late phase (3) where the stage is defined as when the diffuse background fluorescence of the choroidal vein is viewed. A fluorescence agent injected in a vein of an examinee is circulated together with blood so as to first arrive into a thick blood vessel in an eye-ground in the radiographic contrast early phase, and then, the agent gradually penetrates thin blood vessels with time through the medium and the late phase.

Hence, the concentration of the fluorescence agent existing in the blood vessel is higher in the radiographic contrast early phase than that in the radiographic contrast late phase. Accordingly, during taking infrared photofluorography, the examinee eye in the early phase is very bright due to the circulation state of the fluorescence agent in comparison with that in the medium and late phases, and the change in its brightness is also large. Thus, the dynamic range of the fluorescence luminance is largely increased in comparison with that of the image pickup device, so that it is very difficult to uniquely determine the photography light amount and the amplification factor of the image pickup device for obtaining excellent image quality in both the low fluorescence luminance and the high fluorescence luminance.

In order to solve this problem, a technique (a) using an auto gain control (a so-called AGC) was proposed in that while observing the examinee eye, the fluorescence luminance is changed and a constant image signal can be stably obtained. In this technique, during fluorescence observation, the average output of the image signal from the examinee eye is controlled to be stably constant, where even the brightness of the examinee eye and the observing light amount are changed by autonomously changing the amplification factor of the image pickup device. On the other hand, during picking up still images, the luminous period of time of a photography light source is short, several micro seconds, so that even if the AGC is operated, the shooting cannot be tracked. Then, the amplification factor control is changed from the AGC system to a fixed gain system, and the photography light amount is adjusted so as to have an appropriate exposure from the amplification factor of the image pickup device, the observing light amount, and the brightness of the examinee eye before the shooting for stably optimizing the picked up images of the examinee eye.

Also, in order to simply adjust the photography light amount to have appropriate exposure even as the fluorescence luminance in an eye-ground decreases with time after starting the photofluorography, a device and a photography technique (b), both having a timer for detecting an elapsed time after the injection into a vein, are discussed in Japanese Patent Laid-Open No. 2-124137, which describes a photography technique where the photography light emission amount is increased in accordance with the elapsed time after the injection into a vein when the elapsed time signal is received from the timer.

In the related art describing technique (a), during the photofluorography, three operations must be instantly performed, which are: the reading the amplification factor of the AGC during observation direct before the shooting; the calculation of the optimal amplification factor and light emission amount; and the setting of the exposure value. Thus, the workload to be carried out by the ophthalmologic apparatus is large in a period between the starting and completion of the shooting, resulting in a more complicated system.

In the related art describing technique (b), the relationship between the photography elapsed time and the fluorescence luminance in an eye-ground is largely different due to personal factors in equations of an examinee, such as age, sexuality, body weight, body height, and any disease, or the photographic difference due to an examiner, such as the amount of the fluorescence agent to be injected into a vein and the injection rate into the vein. Therefore, in a technique of increasing the photography light amount with only the parameter of the elapsed time after the injection into the vein like this technique, the halation in the radiographic contrast early phase and the contrast shortage in the late phase cannot be avoided, making the shooting difficult.

SUMMARY OF THE INVENTION

At least one exemplary embodiment of the present invention is directed to an ophthalmologic apparatus capable of determining a photography light amount and an amplification factor of an image pickup device.

Additionally, according to an exemplary embodiment of the present invention, an ophthalmologic apparatus includes a light source for illuminating an examinee eye; an image pickup device for picking up fundus images of the examinee eye illuminated with the light from the light source; a memory storing the brightness of the fundus before picking up still image photography and the time when the brightness is detected; and a controller that obtains the change in fundus brightness to a time in response to the instruction of the still image photography on the basis of the fundus brightness and the time when the fundus brightness is detected stored in the memory, and controls the light amount of the light source for taking the still image with the image pickup device on the basis of the fundus brightness obtained from the memory and the obtained change in fundus brightness.

Further features of the present invention will become apparent from the following description of exemplary embodiments with reference to the attached drawings.

DESCRIPTION OF THE EMBODIMENTS

Figure 1:
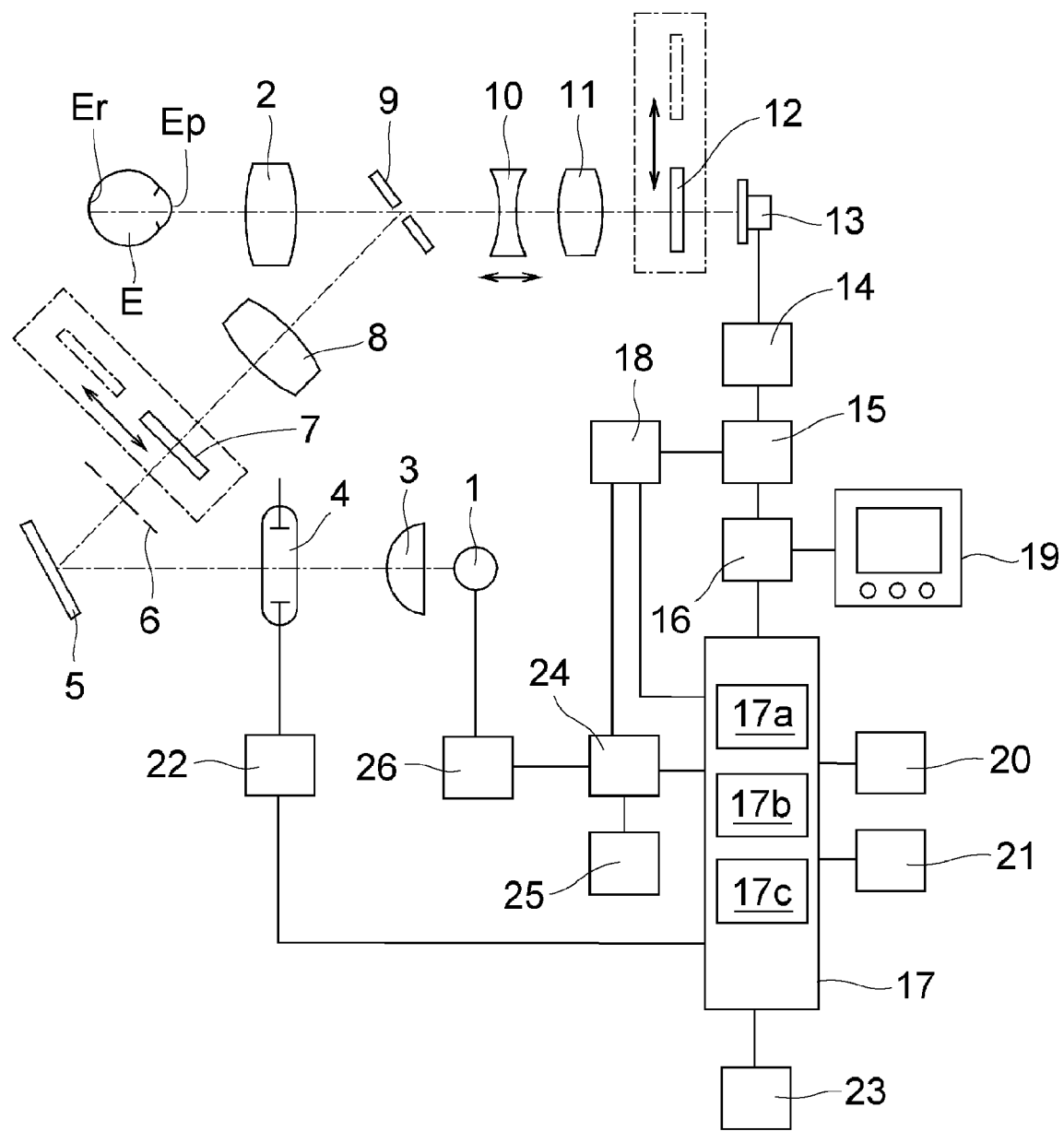
FIG. 1 is a configuration diagram of an exemplary embodiment of the present invention.

An exemplary embodiment of the present invention will be described below.

Exemplary embodiments of the present invention will be described in detail with reference to the exemplary embodiment(s) shown in the drawings.

FIG. 1 is a configuration diagram of a fundus camera. Along an optical path ranging from an observation light source 1 to an object lens 2 opposing an examinee eye E, a condensing lens 3, a photography light source 4, and a mirror 5 are arranged. Furthermore, in a reflection direction of the mirror 5, a diaphragm 6 having an annular opening, an infrared-fluorescence exciter filter 7 arranged insertably/escapably, a relay lens 8, and a perforated mirror 9 are sequentially arranged so as to constitute a fundus illumination optical system.

Along an optical path in the rear of the perforated mirror 9, a fundus observation photography optical system is configured. In the fundus observation photography optical system, a focusing lens 10, a photography lens 11, an infrared-fluorescence barrier filter 12, which is arranged insertably/escapably and blocks the light reflected from the eye ground while transmitting only the exciting light therefrom, and an image pickup device 13 are sequentially arranged.

The output signal of the image pickup device 13 is transmitted to a system control unit 17 via a stored charge reading unit 14, an amplifier 15, and an image-signal processor 16. The amplifier 15 amplifies the image signal with an amplification factor set in an amplification factor control unit 18. The output of the image-signal processor 16 is transmitted to an image display 19 so as to display photography images of the eye-ground of the examinee eye E on the display plane of the image display 19.

The system control unit 17 includes a fundus luminance detecting unit 17a, a luminance change calculating unit 17b, and an optimal exposure determining unit 17c. To the system control unit 17, an amplification factor control unit 18, a photography switch 20, a time measuring unit 21, a photography light source control unit 22, a memory 23, and an observation light amount control unit 24 are also connected. The photography light source control unit 22 controls the brightness of a photography light source 4.

The observation light amount control unit 24 receives the input signal of an observation light amount input unit 25 composed of a variable resister and a tactile switch. The input signal from the observation light amount input unit 25 is for indicating the level of the brightness of the observation light amount, and it stepwise changes at first to ninth levels, for example. The present level of the brightness is displayed on an observation light amount display unit (not shown). The observation light amount control unit 24 is also connected to an amplification factor control unit 18 for controlling the amplification factor of the image pickup device 13 and an observation light source control unit 26 for controlling the light amount of the observation light source 1 so as to output a control signal to the amplification factor control unit 18 and the observation light source control unit 26.

The luminous flux emitted from the observation light source 1 passes through the condensing lens 3 and the photography light source 4 so as to be reflected by the mirror 5. The light reflected from the mirror 5 passes through the diaphragm 6, the infrared-fluorescence exciter filter 7, and the relay lens 8 so as to be reflected by the vicinity of the perforated mirror 9, and then, it passes through the object lens 2 and the pupil EP of the examinee eye E so as to illuminate the fundus Er. The illuminated fundus image passes through the pupil EP of the examinee eye E, the object lens 2, the perforation of the perforated mirror 9, the focusing lens 10, the photography lens 11, and the infrared-fluorescence barrier filter 12 so as to be focused on the image pickup device 13.

The image pickup device 13 holds the stored charge after photo-electric conversion, and the stored charge reading unit 14 outputs the read signal to the image-signal processor 16 via the amplifier 15 while continuously reading the stored charge and clearing the held charge. In addition, the image pickup device 13 has at least a sensibility for observing and filming the radiographic contrast early phase. The image-signal processor 16 applies the output-enabled treatment to the image display 19 so as to display the observed images at that time thereon.

The value established by the observation light amount input unit 25 is inputted into the observation light amount control unit 24. The observation light amount control unit 24 adjusts the amplification factor of the amplification factor control unit 18 in compliance with Table 1, for example, and it controls the voltage to be applied to the observation light source 1 by the observation light source control unit 26.

TABLE 1

| The set value of the observation light amount input unit 25 | The voltage applied to the observation light source 1 | The amplification factor of the amplification factor control unit 18 |
| --- | --- | --- |
| 1 | 0 V | 0 dB |
| 2 | 3 V | 0 dB |
| 3 | 6 V | 0 dB |
| 4 | 9 V | 0 dB |
| 5 | 12 V | 0 dB |
| 6 | 12 V | 3 dB |
| 7 | 12 V | 6 dB |
| 8 | 12 V | 9 dB |
| 9 | 12 V | 12 dB |

That is, when the setting mark of the observation light input unit 25 is 3, the voltage to be applied to the observation light source 1 is 6V, and the amplification factor of the amplification factor control unit 18 is 0 dB. When the setting of the observation light amount input unit 25 is 5, the voltage to be applied to the observation light source 1 stays on 12V, and the amplification factor is 0 dB. Furthermore, when the setting of the observation light amount input unit 25 is 7, the voltage to be applied to the observation light source 1 remains on 12V, and the amplification factor is 6 dB. When the setting is 9, the voltage to be applied to the observation light source 1 remains on 12V, and the amplification factor is 12 dB.

In such a manner, while the fundus Er of the examinee eye E is being observed with appropriate brightness by adjusting the observation light amount input unit 25, the alignment with the examinee eye E using an operating unit (not shown) and the focusing and confirming the photography range by moving the focusing lens 10 are carried out.

According to the exemplary embodiment, in order to display highly fine images with lower noise for an examiner, the observation light amount control unit 24 controls the image pickup device 13 to increase the amplification factor after increasing the value of the observation light source 1 at first in accordance with the increase in setting value of the observation light amount input unit 25.

Figure 2:
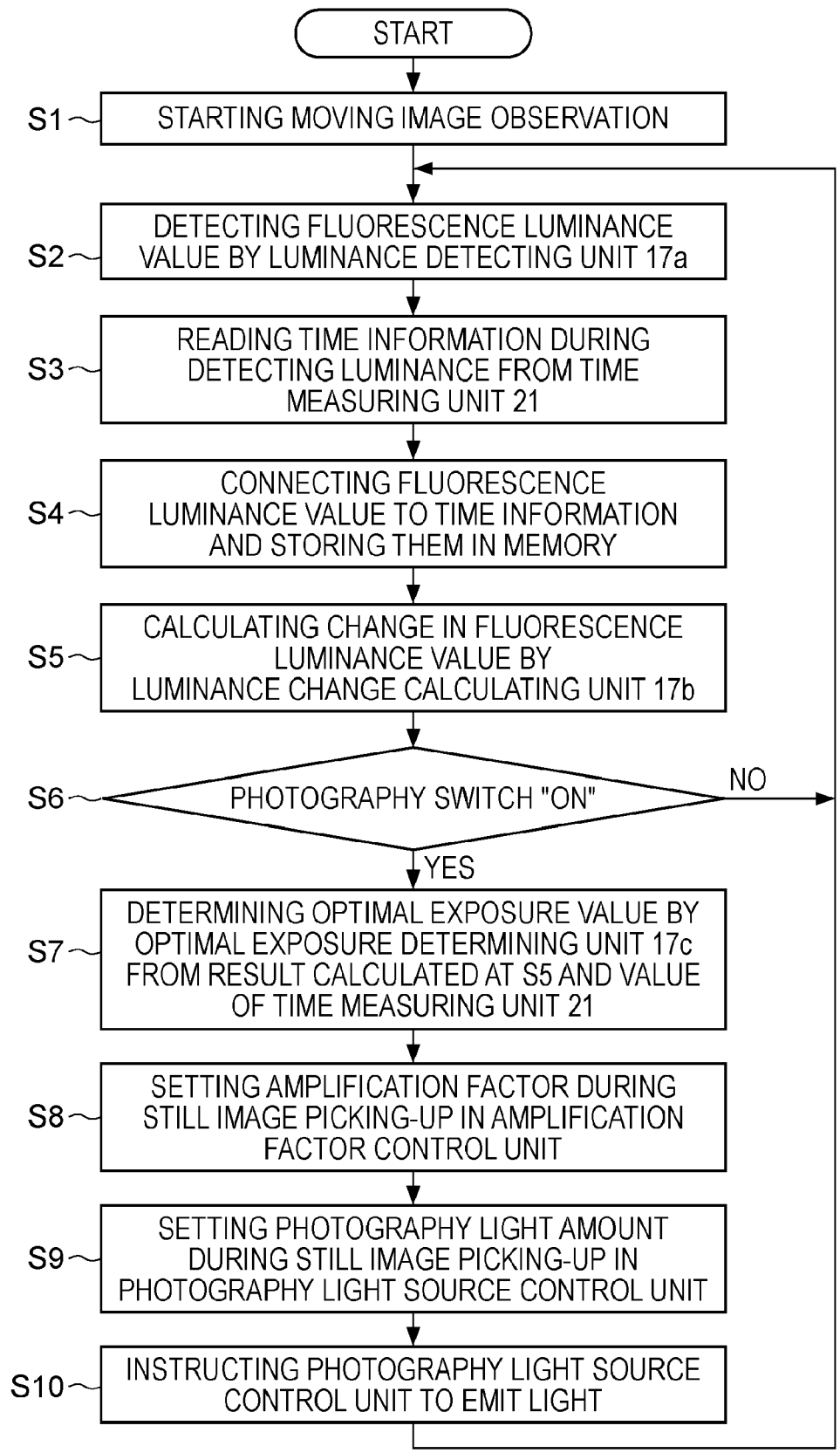
FIG. 2 is an operational flowchart.

FIG. 2 is an operational flowchart of taking infrared photofluorography by an ophthalmologic apparatus. At Step S1, upon detecting an instruction to take moving images from an user, the system control unit 17 starts taking moving images of the fundus Er obtained as fluorescence images by injecting a fluorescence agent for infrared photography into a vein.

Since the fluorescence agent does not approach the fundus Er yet directly after the injection of the fluorescence agent into the vein, there is no light passing through the infrared-fluorescence barrier filter 12 so as to display no image on the image display 19. Hence, it is useful if the maximum scale 9 be established in the observation light amount input unit 25 until the fluorescence agent is circulated around the fundus Er. Then, it is useful if a user suitably adjust the brightness of the image display 19 by the observation light amount input unit 25 in accordance with the fluorescence excitation in the fundus Er.

The display of the moving images taken by the image pickup device 13 herein is in fact a continuous display of still images displayed at predetermined time intervals. Generally, the image display is continuously switched at speeds of 15 to 30 frames/second. However, for distinguishing it from the still image photography using the photography light source 4 according to the exemplary embodiment, the images using the observation light source 1 are described as "moving images."

At Step S2, on the basis of the fundus fluorescence images obtained from the image-signal processor 16 and the information of the observation light amount control unit 24, the fundus luminance detecting unit 17*a* detects the fluorescence luminance value every one frame or at intervals of adequate frames. The fluorescence luminance value herein indicates the fundus brightness due to the circulating load of the fluorescence agent.

The larger the luminance value of the fundus fluorescence images obtained from the image-signal processor 16 is in addition to the smaller the setting value of the observation light amount control unit 24 is, the fundus luminance detecting unit 17*a* determines the fluorescence luminance value to be larger. According to the exemplary embodiment, a table is stored in the memory 23 for obtaining the fluorescence luminance value using the luminance value of the fundus fluorescence images obtained from the image-signal processor 16 and the setting value of the observation light amount control unit 24 as parameters.

At Step S3, the system control unit 17 obtains the time when the fluorescence luminance value is detected by the fundus luminance detecting unit 17 *a* from the time measuring unit 21.

At Step S4, into the memory 23, the system control unit 17 stores the fluorescence luminance value obtained at Step S2 and having the time information obtained at Step S3 added thereto. At Step S5, the luminance change calculating unit 17*b* calculates the present amount of change in fluorescence luminance value on the basis of the fluorescence luminance value stored in the memory 23 and the time interval information after the time when the fluorescence luminance value is previously detected.

At Step S6, an examiner performs the alignment while viewing the picture of the image display 19 so as to push the photography switch 20 when the alignment is made. The system control unit 17 repeats the processes of Step S2 to Step S5 until the pushing down of the photography switch 20 by the examiner is detected.

A noon-limiting example of a control method that can be used in the exemplary embodiment is to forecast the fluorescence luminance value (the fundus brightness) at the time when the photography switch 20 is pushed, while observing moving images having a small system load, on the basis of the information about the fundus brightness before the photography switch 20 is pushed.

Figure 3:
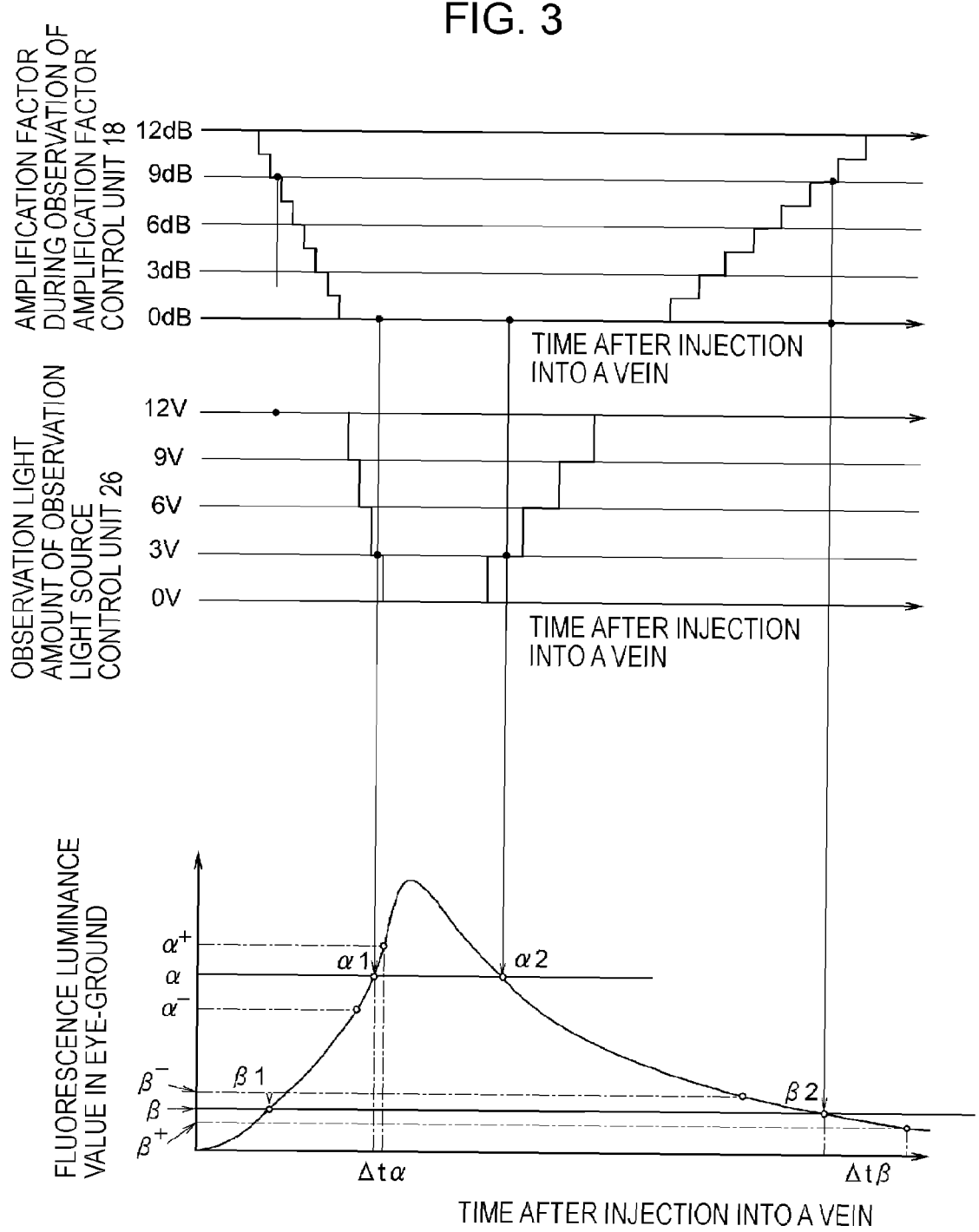
FIG. 3 is an explanatory view of amplification factors of an image pickup device during observing moving images in an elapsed time after injection of a fluorescent agent into a vein and luminance values of an eye-ground due to an observation light amount and fluorescence light.

FIG. 3 shows the amplification factors of the image signal outputted from the image pickup device 13, which are controlled by the amplification factor control unit 18 so as to have a substantially constant brightness of the fundus Er displayed on the image display 19, the voltage values to be applied to the observation light source 1, and the fluorescence luminance values in the fundus Er. The fundus luminance detecting unit 17*a*, stores in the memory 23, a relative table with the observation light amount from the input unit 25 and the fluorescence luminance value in the fundus Er as the output.

By the amplification factor of the image signal outputted from the image pickup device 13 and the voltage value to be applied to the observation light source 1, the displayed fundus brightness can be controlled to be constant without depending on the change in fluorescence luminance value as shown in FIG. 3. For example, when the amplification factor is 9 dB and the voltage value to be applied to the observation light source 1 is 12V, the luminance value in the fundus is $\beta$; and further when the amplification factor is 0 dB and the voltage value to be applied to the observation light source 1 is 3V, the luminance value in the fundus is $\alpha$.

In characteristics of the fluorescence luminance value in the fundus Er, toward the radiographic contrast early phase from directly after the injection in a vein, with increasing fluorescence density in the fundus Er, the fluorescence luminance value is rapidly increased. Then, in the contrast late phase after passing across a certain peak, with decreasing fluorescence density, the fluorescence luminance value is gradually decreased. Hence, the fundus luminance values $\alpha$ and $\beta$ respectively determined in the same amplification factor and observation light amount are considered to be two cases of $\alpha 1$ and $\beta 1$ during increasing the fluorescence density and $\alpha 2$ and $\beta 2$ during decreasing the fluorescence density. However, in view of the luminance value directly before being stored in the memory 23, the respective fundus luminance values $\alpha$ and $\beta$ can be uniquely determined.

For example, the fundus luminance value $\alpha$ has possibilities of values $\alpha 1$ and $\alpha 2$ from the same amplification factor and observation light amount. Since when the predecessor fluorescence luminance value is $\alpha^-$, $\alpha > \alpha^-$, the luminance value $\alpha$ is uniquely determined to be the luminance value $\alpha 1$ during the increasing. Furthermore, with regard also to the luminance value $\beta$, since $\beta < \beta^-$, the luminance value $\beta$ is determined to be the luminance value $\beta 2$ during the decreasing.

Figure 4:
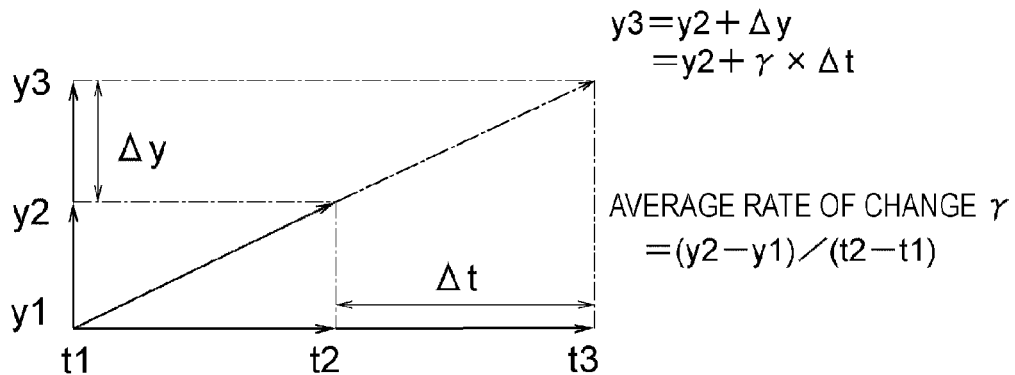
FIG. 4 is a graph for calculating an average rate of change in a luminance-change calculating unit.

FIG. 4 shows a calculating method of the amount of change in luminance from the primary average rate of change. The average rate of change $\gamma$ is expressed by:

$$\gamma = (y2 - y1)/(t2 - t1),$$

where y1 is the fluorescence luminance value in the fundus Er obtained from the fundus luminance detecting unit 17*a*; t1 is the time when the luminance value y1 is detected; and t2 is the time when the luminance value is y2.

When the system control unit 17 detects that the photography switch 20 is pushed at the time $t3 = (t2 + \Delta t)$, the fundus luminance value y3 at that time can be calculated by $y3 = y2 + \Delta y = y2 + \gamma \times \Delta t$, where $\Delta t$ is sufficiently small.

In FIG. 3, the luminance values $\alpha$ and $\beta$ are uniquely determined by a luminance detector. Hence, the luminance values $\alpha^+$ and $\beta^+$ at times after $\Delta t\alpha$ and $\Delta t\beta$ seconds are expressed by $\alpha^+ = \alpha + \gamma\alpha \times \Delta t\alpha$, and $\beta^- = \beta + \gamma\beta \times \Delta t\beta$, respectively, from the luminance change calculating unit 17*b*, where $\gamma\alpha$ and $\gamma\beta$ are the average rates of change obtained from $\alpha^-$ and $\beta^-$, respectively. Thereby, the fluorescence luminance value in the fundus Er when the pushing of the photography switch 20 is detected can be calculated from the luminance change calculating unit 17*b* and the time measuring unit 21.

That is, from the calculated results of the fluorescence luminance value obtained from the processes Step S2 to S5 of FIG. 2 and by reading the time when an examiner pushes the photography switch 20 in the time measuring unit 21, the fluorescence luminance value in the instant of pushing the photography switch 20 at Step S6 can be readily obtained.

Figure 5:
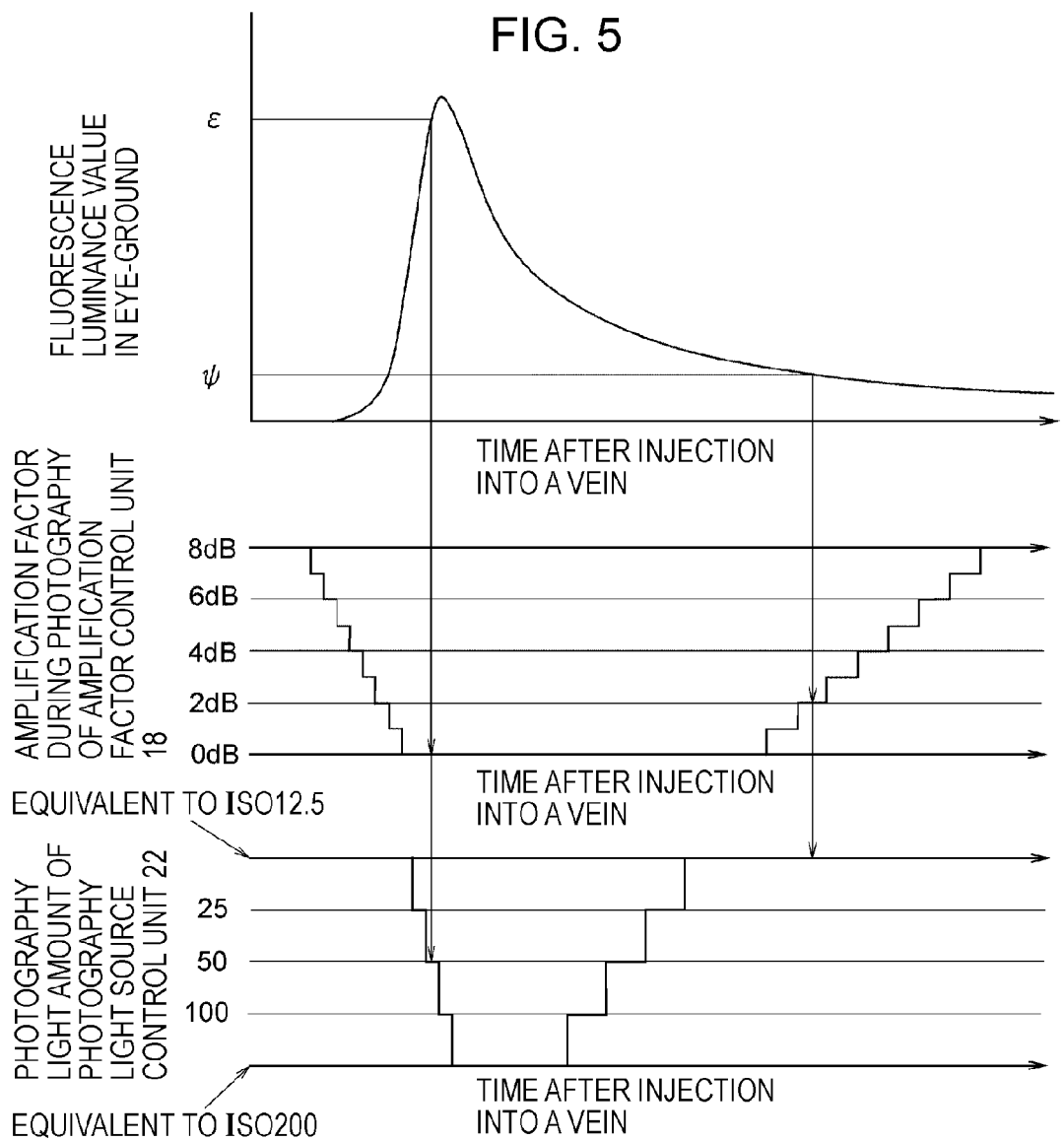
FIG. 5 is an explanatory view for determining an amplification factor of the image pickup device during picking up still images and a photography light amount in an optimal exposure determining unit from the fluorescence luminance value of an eye-ground.

FIG. 5 shows that at Step S7, the system control unit 17 obtains the amount of light emission of the photography light source 4 and the amplification factor of the image pickup device 13 from the fluorescence luminance value of the fundus Er determined by the optimal exposure determining unit 17*c*.

The present exemplary embodiment provides an examiner with highly fine photographic images with lower noise. Hence, during observing moving images, the system control unit 17, in the same way as in the observation light amount control unit 24, has priority to control lighting in the setting light amount value of the photography light source 4 without increasing the amplification factor of the still image signal.

The system control unit 17 correctively controls the amplification factor of the still image signal with the fundus luminance uncontrollable by only adjusting the photography light amount.

That is, when the fluorescence luminance value of the fundus Er starts increasing by the circulation of a fluorescence agent, the system control unit 17 lowers the control value of the amplification factor at first, and after the value is lowered to the lowest value, it lowers the illumination light amount of the photography light source 4. Conversely, when the luminance value begins decreasing, the system control unit 17 increases the illumination light amount of the photography light source 4 at first, and after the value is increased to the highest value, it increases the control value of the amplification factor. The control range of the amplification factor of the image pickup device 13 in this non-limiting example herein is within 0 dB to 8 dB, and the output of the photography light source 4 is changeable between ISO200 equivalent and ISO12.5 equivalent.

As shown in FIG. 5, upon obtaining the fluorescence luminance value, the optimal exposure determining unit 17c uniquely determines the optimal amplification factor and photography light amount from the fluorescence luminance value according to the control method described above. For example, when the luminance value is $\epsilon$, the photography light amount and the amplification factor are ISO050 equivalent and 0 dB, respectively. When the luminance value is $\phi$, the photography light amount and the amplification factor control value are ISO12.5 equivalent and 2 dB gain, respectively.

At Step S8 of FIG. 2, the system control unit 17 establishes the amplification factor obtained at Step S7 in the amplification factor control unit 18. Also, at Step S9, the system control unit 17 establishes the photography light amount obtained at Step S7 in the photography light source control unit 22. Furthermore, at Step S10, the system control unit 17 instructs the photography light source control unit 22 to emit light so as to control the execution of the still image photography.

After the completion of series of photography operations, the amplification factor of the amplification factor control unit 18 is reestablished to be the value immediately before picking up still image(s) so as to complete the photography operations. After the completion of the photography operations, the process is returned to Step S2 so as to observe moving images.

According to the exemplary embodiment, two values of the amplification factor and the photography light amount are established at Steps S8 and S9, respectively; alternatively any one of the values may be established. Also, according to the exemplary embodiment, after the completion of the photography, the picked up images are not recorded; however, the images may be recorded. That is, the read image signal is amplified in the amplifier 15 and converted into the digital signal by an A/D converter (not shown) via the image-signal processor 16 so as to enter the system control unit 17. Then, the converted digital image signal is recorded on an image recorder (not shown) connected to the system control unit 17.

The image recorder herein may use a recording medium such as a hard disk, MO, Zip, Jazz, CD-R/RW, DVD-RAM, DVD-R/RW, semiconductor memory, or any other type of recording and/or data storage medium as known by one of ordinary skill in the relevant arts.

Furthermore, according to the exemplary embodiment, the fluorescence luminance value for the next photography is obtained by obtaining the average rate of change from the moving image information of two points at Step S2 of FIG. 2; alternatively, the fluorescence luminance value for the next photography may be obtained from a plurality of pieces of moving image information using exponential approximation and polynomial approximation.

According to the exemplary embodiment, the luminance detection and the change in luminance are obtained from the moving images so as to calculate the fluorescence luminance value for the next photography; alternatively, when the photography interval is sufficiently short, the luminance can be detected from continuous still images so as to calculate the fundus luminance value for the next photography by obtaining the change in luminance.

According to the exemplary embodiment, the appropriate photography light amount and amplification factor of the image pickup device can be uniquely determined during the fluorescence photography by calculating the change in fluorescence luminance so as to always anticipate the fundus luminance value, thereby obtaining still images without failure.

During observing the fluorescence with a small load to the apparatus, the change in fluorescence luminance can be calculated, so that the load applied to the apparatus at the photography moment can be dispersed, thereby stably taking pictures in an inexpensive apparatus without using an expensive apparatus.

As described above, in the ophthalmologic apparatus according to the exemplary embodiment, the photography light amount and the amplification factor of the image pickup device, which can be used for the fluorescence photography, can be determined by obtaining the change in fundus brightness.

While the present invention has been described with reference to exemplary embodiments, it is to be understood that the invention is not limited to the disclosed exemplary embodiments. The scope of the following cm claims is to be accorded the broadest interpretation so as to encompass all modifications, equivalent structures and functions.

This application claims the benefit of Japanese Application No. 2005-333627 filed Nov. 18, 2005, which is hereby incorporated by reference herein in its entirety.

What is claimed is:

1. An ophthalmologic apparatus comprising:
    a light source configured to illuminate an examinee eye;
    an image pickup device configured to pick up fundus images of the examinee eye illuminated with the light from the light source;
    a memory storing the brightness of the fundus before picking up a still image and a time when the brightness is detected; and
    a controller that forecasts a fundus brightness at the time when the still image is picked up based on the fundus brightness obtained from the memory and an obtained change in fundus brightness and controls the light amount of the light source for picking up the still image with the image pickup device on the basis of the forecasted brightness of the fundus.

2. The apparatus according to claim 1, wherein the controller controls the amplification factor of an image signal outputted from the image pickup device.

3. A control method of an ophthalmologic apparatus comprising the steps of:
    storing the brightness of a fundus and the time when the fundus brightness is detected in a memory;
    detecting the instruction of picking up a still image;
    forecasting a fundus brightness based on the fundus brightness obtained from the memory and an obtained change in fundus brightness and;
    controlling the light amount of a light source for picking up the still image with the image pickup device on the basis of the forecasted brightness of the fundus.

* * * * *